United States Patent [19]

Webb

[11] 4,329,496
[45] May 11, 1982

[54] METHOD FOR MAKING AROMATIC BIS(ETHER PHTHALIC ACID) OR AROMATIC BIS(ETHER ANHYDRIDE)

[75] Inventor: Jimmy L. Webb, Saratoga, N.Y.

[73] Assignee: General Electric Company, Schenectady, N.Y.

[21] Appl. No.: 250,994

[22] Filed: Apr. 3, 1981

[51] Int. Cl.$^3$ .................. C07D 307/89; C07C 65/24
[52] U.S. Cl. .................. 562/468; 562/429; 562/432; 562/460; 562/469; 562/473; 549/241
[58] Field of Search .................. 260/346.3; 562/460, 562/473, 468, 469, 429, 432

[56] References Cited

U.S. PATENT DOCUMENTS 3,931,243  1/1976  Paustian et al. .................. 260/346.7
4,116,980  9/1978  Webb .................. 260/346.3

*Primary Examiner*—Henry R. Jiles
*Assistant Examiner*—Bernard Dentz
*Attorney, Agent, or Firm*—Peter A. Bielinski; James C. Davis, Jr.; Joseph T. Cohen

[57] ABSTRACT

A method is provided for converting aromatic bis(ether N-organo substituted phthalimides) to aromatic bis(ether anhydrides) by heating a bisphasic aqueous-organic mixture of aromatic bis(ether N-organo substituted phthalimide), phthalic anhydride and an exchange catalyst to effect an imide-anhydride exchange producing an aqueous phase containing aromatic bis 4ether phthalic acid) and an organic phase containing N-organo substituted phthalimide. The aromatic bis(ether phthalic acid) is then optionally dehydrated to the corresponding anhydride.

15 Claims, 2 Drawing Figures

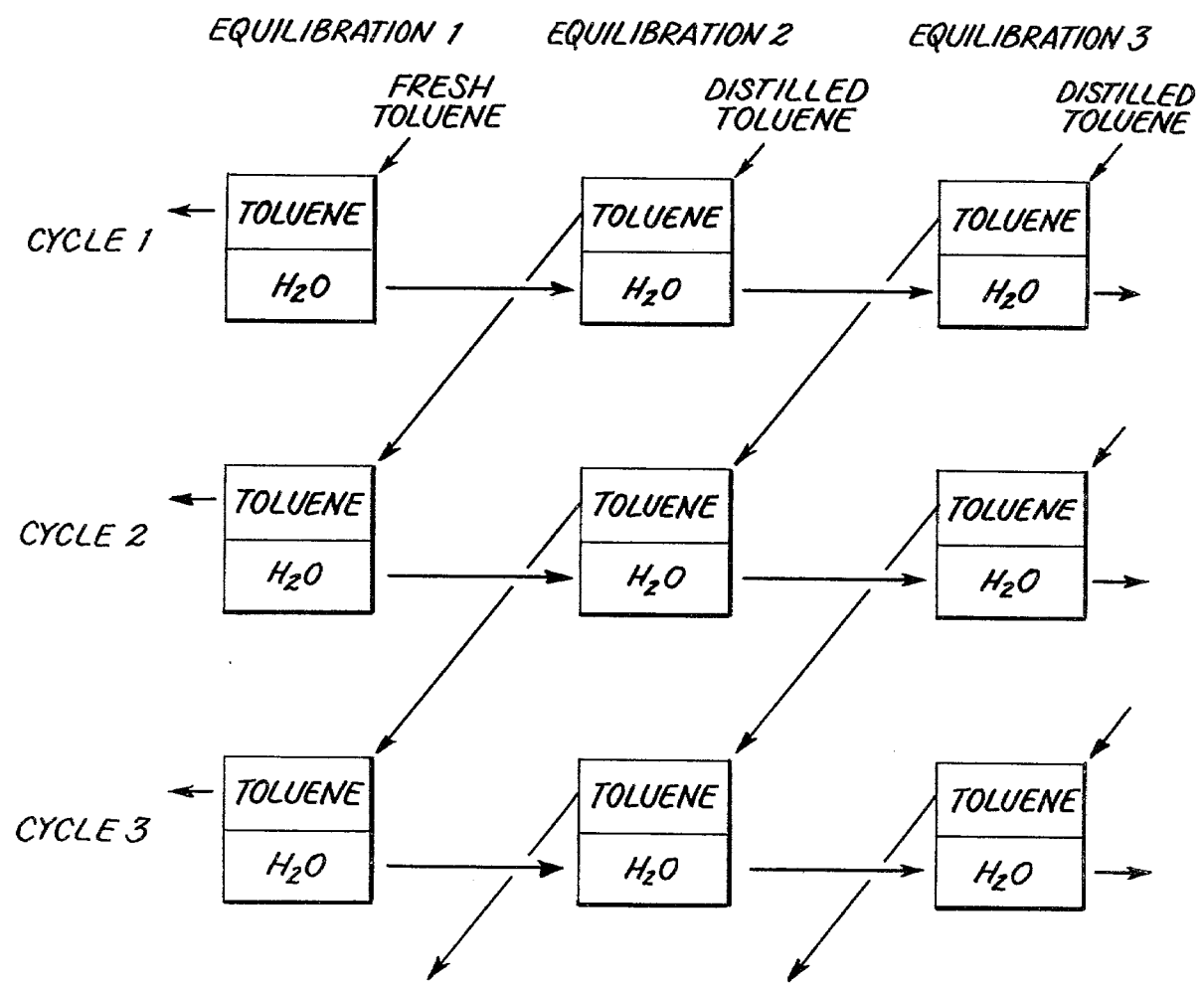

METHOD FOR MAKING AROMATIC BIS(ETHER PHTHALIC ACID) OR AROMATIC BIS(ETHER ANHYDRIDE)

CROSS REFERENCE TO RELATED APPLICATIONS

Reference is made to copending application Ser. No. 251,019 filed Apr. 3, 1981 of Jimmy L. Webb and Donald L. Phipps, for Method for Making Aromatic Bis(Ether Anhydride)s, copending application Ser. No. 250,804 filed Apr. 3, 1981 of Jimmy L. Webb, for Method for Making Aromatic Bis(Ether Anhydride)s, and copending application Ser. No. 253,446 filed Apr. 13, 1981 of Jimmy L. Webb and Bharat M. Mehta for Method for Making Aromatic Bis (Ether Anhydride), all of which are assigned to the same assignee as the present invention.

BACKGROUND OF THE INVENTION

Prior to the present invention as shown by Heath, et al. U.S. Pat. Nos. 3,879,428 and 3,957,862, assigned to the same assignee as the present invention, aromatic bis(ether anhydrides) (hereinafter referred to as "bisanhydrides") of the general formula:

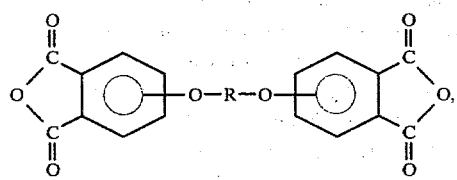

were made by a multi-step procedure involving the base hydrolysis of an aromatic bis(ether N-organo substituted phthalimide) of the formula:

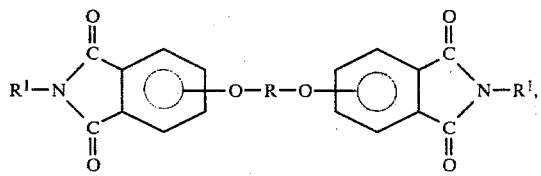

A more specific compound of which is 2,2-bis[4-(3,4-dicarboxy)phenyl]propane bis-N-methylimide which has the formula:

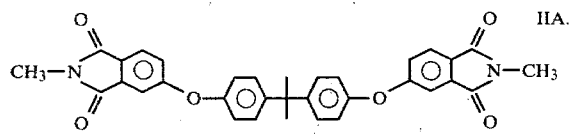

where R is a divalent aromatic radical having from 6–30 carbon atoms and $R^1$ is a monovalent organic radical selected from the class consisting of $C_{(1-8)}$ alkyl radicals, and organic radicals, having from 6–20 carbon atoms, for example, aromatic hydrocarbon radicals and halogenated derivatives thereof. This procedure produced a tetra-acid salt which was thereafter acidified to the tetra-acid followed by the dehydration of the tetra-acid to produce the aromatic bis(ether anhydride) of formula I.

Although the procedure of Heath, et al. provides a valuable route to both the aromatic bis(ether phthalic acids) and aromatic bis(ether phthalic anhydrides) it requires the base hydrolysis of the aromatic bis(ether N-organo substituted phthalimide of formula II and the conversion of the resulting salt to the tetra-acid, followed by the dehydration of the tetra-acid. In addition to requiring a variety of steps to convert the bisimide to a bisanhydride, inorganic salts are generated causing disposal problems. Efforts, are, therefore, being directed to providing a more simplified procedure for making the bisanhydride of formula I, or its tetra-acid precursor.

Markezich, et al. U.S. Pat. No. 4,128,574 discloses an imide-anhydride exchange reaction resulting in the production of organic polycarboxylic acids, anhydrides thereof, or organic imides. For example, in particular instances, a bisimide of formula IIA, is heated with phthalic anhydride in the presence of water to effect an exchange between the aforementioned bisimide and the phthalic anhydride to provide the corresponding tetra-acid or anhydride thereof.

Although the Markezich, et al. method eliminates many of the disadvantages of the prior art, such as, the formation of inorganic salts and the requirement of a multi-step procedure, Markezich, et al. is essentially a batch method. The recovery of a tetra-acid or bisanhydride at a satisfactory yield, 80% or higher concentration, requires several heating and stripping cycles. It is also difficult to achieve substantial conversion of the bisimide to the tetra-acid or the bisanhydride without resort to the recycling of excessive amounts of phthalic acid or phthalic anhydride. Based on the nature of the exchange between the bisimide and phthalic acid or phthalic anhydride, optimum conversion cannot be realized unless the N-organo phthalimide of the general formula:

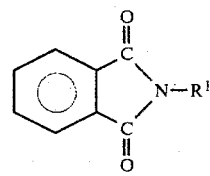

where $R^1$ is as previously defined, which is also formed in the reaction, is separated from the mixture.

Webb, in U.S. Pat. No. 4,116,980, showed that optimum conversion of the bisimide to the tetra-acid or dianhydride thereof, can be achieved based on the imide-anhydride exchange in the presence of water, as shown by the following:

$$A + B \rightleftharpoons A' + B',$$

where A and A' are imides and B and B' are anhydrides, if the A' imide is selectively removed from the reaction during the exchange. For example, in the above equation, A can be a bisimide, B can be a phthalic acid, B' can be a bis anhydride or tetra-acid and A' can be an N-organo phthalimide. Webb achieved these results by venting a portion of the vapor phase of the reaction mixture consisting of a liquid phase and a vapor phase during the exchange. The vapor phase consisted essentially of water and N-organo phthalimides with very little phthalic acid so that by continuously venting the vapor phase during the exchange, the reaction is driven to the right. It is, therefore, possible to convert the starting bisimide to the corresponding tetra-acid or bis anhydride without either shutting down the reactor or recycling excessive amounts of phthalic acid.

DETAILED DESCRIPTION OF THE INVENTION

Figure 1:
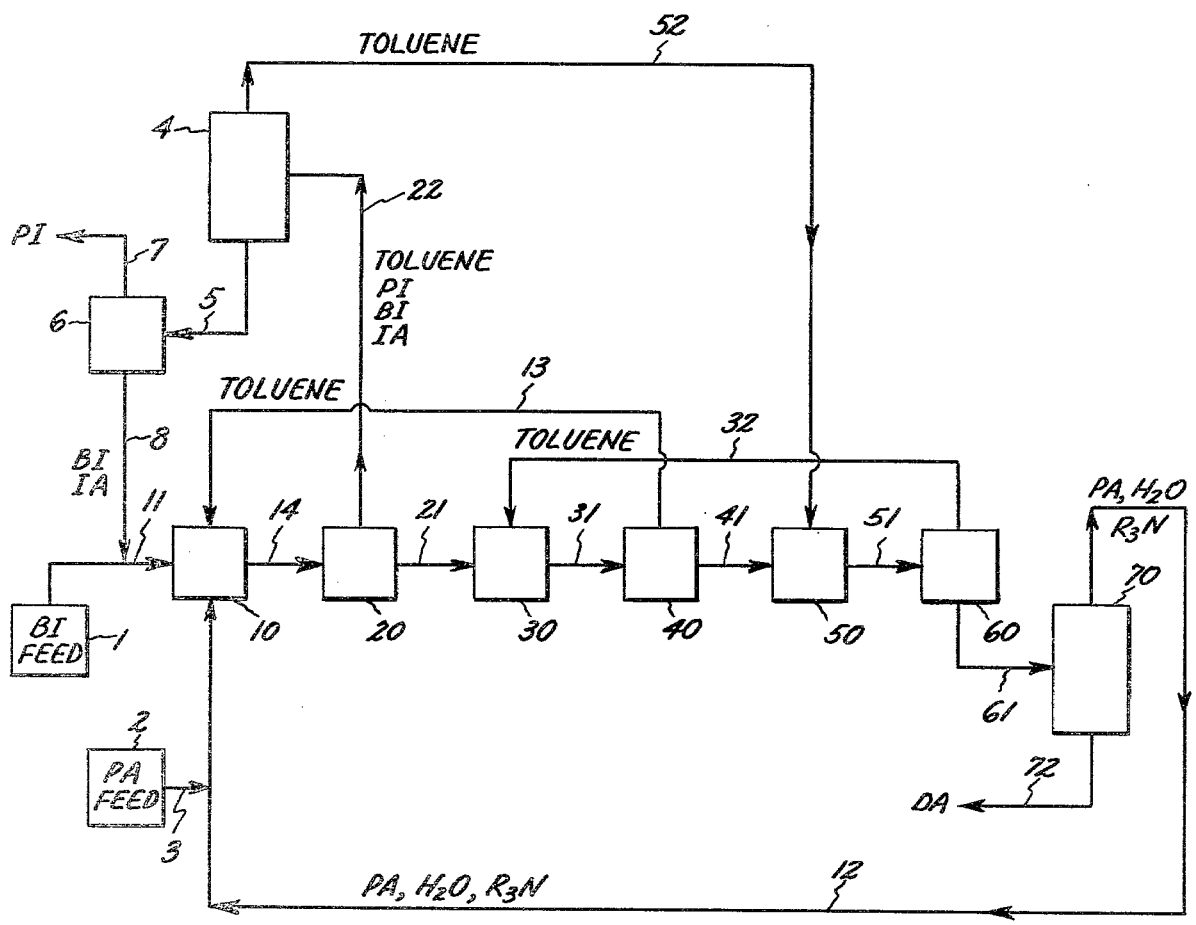

The present invention is based on the development of a new biphasic imide-anhydride exchange process in which an inert organic solvent solution of an aromatic bis(ether N-organo substituted phthalimide) hereinafter also identified as "BI" is contacted with an aqueous solution of phthalic acid hereinafter also identified as "PA" and an exchange catalyst at an elevated temperature. Imide-anhydride exchange occurs and a major portion of the bis-compound moves from the organic phase to the aqueous phase where it exists as the salt of the aromatic bis(ether phthalic acid) hereinafter also identified as "TA" of the general formula:

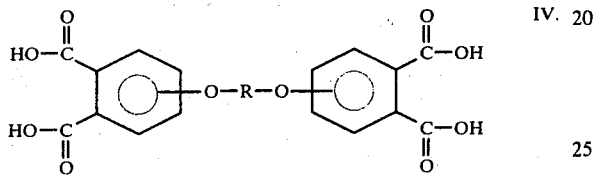

IV.

where R is as previously defined. This compound is easily converted by conventional means to the aromatic bis(ether phthalic anhydride) hereinafter also identified as "DA" of formula I. The N-organo phthalimide hereinafter also identified as "PI" formed by the exchange moves out of the aqueous phase and into the organic phase thereby facilitating an increased conversion of the BI to the TA. Unreacted (excess) phthalic acid remains in the aqueous phase as a salt.

Before the exchange reaction, all imides (PI and BI) exist in the organic phase and all acids and catalysts exist in the aqueous phase. After the exchange reaction, when equilibration is established, the major portion of the BI has moved from the organic phase to the aqueous phase where it exists as a salt of the TA. The phthalic imide, hereinafter also identified as "PI", formed by the exchange moves into the organic phase along with the unreacted BI and some aromatic bis(ether N-organo substituted phthalimide ether anhydride) hereinafter identified as "IA" of the general formula:

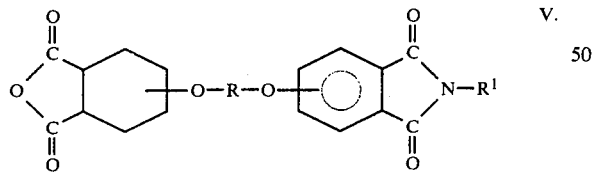

V.

where R and R' are as previously defined. Therefore, at equilibrium except for a small amount of IA present in both phases, the original condition, with all imides being present in the organic phase and all acids or salts of the acids being present in the aqueous phase, still exists.

Corrosion problems associated with previous methods can be substantially eliminated by neutralization of all acids by using an amine catalyst and in addition the biphasic exchange process makes possible a clean separation of the N-organo phthalimide from the phthalic acid. The exchange can also be rapidly catalyzed, requires substantially less process energy than the previous methods and conserves reactants, solvents and catalyst.

There is provided by the invention a biphasic imide-anhydride exchange process for making aromatic bis(ether phthalic acid) from aromatic bis(ether phthalamide) which comprises, (A) heating at an elevated temperature, e.g., from 170°–260° C. and under superatmospheric pressure, e.g., between 200–500 psi, a mixture comprising:
  (i) aromatic bis(ether phthalimide) of formula II
  (ii) 2–20 moles of phthalic anhydride or phthalic acid per mold of (i),
  (iii) a sufficient and effective amount of an exchange catalyst,
  (iv) 0.01–100 parts of water per part, by weight, of (i),
  (v) 0.01–100 parts of a water-immiscible inert organic solvent per part, by weight, of (i), to produce an equilibrated liquid biphasic reaction mixture, comprising an aqueous phase having selectively dissolved therein, the aromatic bis(ether phthalic acid) formed in the exchange reaction, the exchange catalyst together with any unreacted phthalic acid, and an organic phase having selectively dissolved therein, N-organo substituted phthalimide of formula III which was also formed in the exchange reaction, together with any unreacted aromatic bis(ether phthalimide), (B) separating the organic phase from the aqueous phase, and (C) recovering the aromatic bis(ether phthalic acid) from the aqueous phase.

Radicals included by R are for instance,

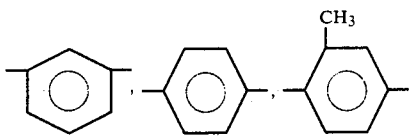

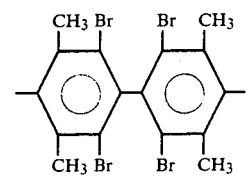

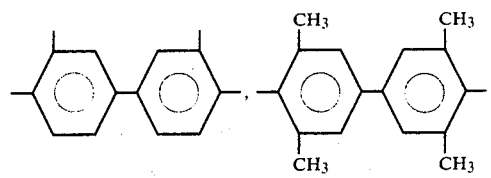

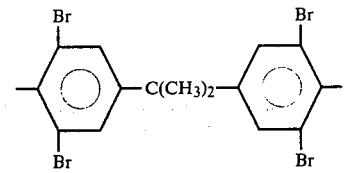

and divalent organic radicals of the general formula:

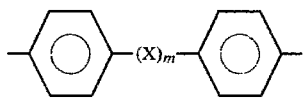

where X is a member selected from the class consisting of divalent radicals of the formulas, $-C_yH_{2y}$,

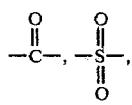

—O—, —S—, where m is 0 or 1, and y is a whole number from 1 to 5 inclusive.

Radicals included by $R^1$ are for example, phenyl tolyl, xylyl, naphthyl, chlorophenol, bromonaphthyl, etc. and alkyl radicals, such as methyl, ethyl, propyl, etc.

The bisimides of formula II and a method for making them, are more particularly described in the aforementioned U.S. Pat. No. 3,879,428, Wirth et al., which is based on the initial formation of N-organo substituted phthalimide of the formula:

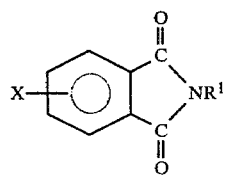

VI.

where X is a radical selected from the class consisting of nitro, halo, e.g. chloro, fluoro, bromo, etc., and $R^1$ is as previously defined. The phthalimide of formula VI can be formed by effecting a reaction between X- substituted phthalic anhydride and an organic amine, such as aniline, toluidine, methyl amine, ethyl amine, etc.

Included by the phthalimides of formula VI are, for example, N-methyl-4-nitrophthalimide, N-phenyl-3-nitrophthalimide, N-phenyl-4-nitrophthalimide, N-methyl-3-nitrophthalimide, N-butyl-4-nitrophthalimide, etc. As further shown in U.S. Pat. No. 3,879,428, the aromatic bis(ether phthalimide)s of formula II can be made by effecting reaction between phthalimides of formula VI and an alkali diphenoxide of the general formula:

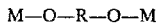 M—O—R—O—M (VIII)

where R is as previously defined, and M is a metal ion of an alkali metal for example, sodium, potassium, lithium, etc.

Included by the alkali diphenoxides of formula VII, are sodium and potassium salts of the following dihydric phenols.
2,2-bis(2-hydroxyphenyl)propane;
2,4'-dihydroxydiphenylmethane;
bis-(2-hydroxyphenyl)methane;
2,2-bis-(4-hydroxyphenyl)propane hereinafter identified as "Bisphenol-A" or "BPA",
1,1-bis-(4-hydroxyphenyl)ethane;
1,1-bis-(4-hydroxyphenyl)propane;
2,2-bis-(4-hydroxyphenyl)pentane;
3,3-bis-(4-hydroxyphenyl)pentane;
4,4'-dihydroxybiphenyl;
4,4'-dihydroxy-3,3,5,5'-tetramethylbiphenyl;
2,4'-dihydroxybenzophenone;
4,4'-dihydroxydiphenylsulfone;
2,4'-dihydroxydiphenylsulfone;
4,4'-dihydroxydiphenyl sulfoxide;
2,4'-dihydroxydiphenyl sulfoxide;
4,4'-dihydroxydiphenyl sulfide;
hydroquinone;
resorcinol;
3,4'-dihydroxydiphenylmethane;
4,4'-dihydroxydenzophenone;
4,4'-dihydroxydiphenylether, etc.

Exchange catalysts which can be employed in the invention are; acids such as sulfuric, phosphoric, hydrochloric, methanesulfonic, fluoroboric, toluenesulfonic, acetic butyric, trifluoroacetic acids, etc.; metal salts, such as $FeCl_3$, $ZnCl_2$, $SnCl_4$, $AlCl_3$ and their bromides; trialkyl amines hereinafter also identified as "$R_3N$", such as trimethylamine, triethylamine, tripropylamine, tributylamine, etc. with the preferred catalysts being triethylamine and trimethylamine.

Organic solvents which can be used in the invention are inert, water immiscible solvents which selectively dissolve any imide compounds present initially or formed during the exchange reaction for example, toluene, benzene, xylene, chlorobenzene and orthodichlorobenzene.

The following broad and preferred parameters have been determined for the biphasic imide-anhydride process:

| | | |
|---|---|---|
| 1. | Temperature | Range 170°–260° C. |
| | | Preferred 185°–225° C. |
| 2. | Pressure | Determined by temperature |
| | | Range 200–500 psi |
| 3. | PA to BI Mole Ratio | Range 2:1 to 20:1 |
| | | Preferred 4–6:1 |
| 4. | Catalyst to PA Mole Ratio | Range 1:1 to 3:1 |
| | | Preferred ~ 2:1 |
| 5. | Organic solvent to water weight ratio | Range 0:1 to 10:1 |
| | | Preferred ~ 4:1 |
| 6. | Solids Content | Range 1% to 70% |
| | | Preferred ~ 10–15% |

A more complete understanding of the practice of the present invention can be obtained by reference to the drawing.

In FIG. 1, there is shown a continuous three step imide-anhydride exchange process incorporating the method of the present invention which produces 2,2-bis 4-(3,4-dicarboxyphenoxy)phenyl propane of at least 97 mole percent purity by effecting the imide-anhydride exchange between PA and BI in the presence of an organic solvent which selectively absorbs the imide, separating and removing the organic phase, then repeating the equilibration-separation two more times with organic solvent to prouce TA in the aqueous phase. The organic phase is used in the third, second then first equilibration-separation steps after which it is distilled to remove the imides and returned to the third equilibration step and recycled. Of the imides removed during the distillation PI is recovered and can be nitrated and used to produce more BI, while the remaining BI and IA are recycled. After recovery of the TA from the aqueous phase by distillation of $H_2O$, $R_3N$ and unreacted PA these materials are recycled to the first equilibration step.

More particularly, there is shown at 10, the first equilibration vessel, in which an aqueous solution of excess PA and two moles of R₃N catalyst per mole of PA is heated together with a toluene solution of BI. Phthalic acid (PA) or phthalic anhydride is fed to 10 via line 3 from a PA resevoir 2 along with recycled water, R₃N and any unreacted PA from the previous cycle via line 12. Toluene is recycled from step 2 of the previous cycle via line 13. BI feed stock is fed from resevoir 1 via line 11 to the first equilibration vessel 10 along with unreacted BI and partially reacted IA which are separated from the toluene in stills 4 and 6 and transferred via lines 5 and 8. The two phases are heated together at approximately 200° C. and 300-500 lbs. per square inch pressure, depending upon the exact temperature, for 1 to 2 hours to produce a mixture which is chemically equilibrated.

At this time, the mixture is pumped from equilibration vessel 10 via line 14 to the first step phase separator or decantor 20. While still hot, the mixture is allowed to settle and separate, the tolune phase is drawn off and pumped via line 22 to a first distillation unit 4 in which the toluene is stripped off and condensed for subsequent recycling. The still bottom from 4, containing BI, IA and PI are pumped via line 5 to a second still 5 where PI is distilled off for possible subsequent production of BI. The still bottoms from 6 containing BI and IA are recycled via line 8 to the first equilibration vessel 10. The aqueous phase from the first step phase separator 20 is pumped via line 21 to a second equilibration vessel 30 where it is mixed with toluene decanted from the third step phase separator 60. When equilibration is achieved in the second equilibration vessel 30, the mixture is pumped via line 31 to the second step phase separator 40 where, after settling, the toluene layer is returned to the first equlibration vessel 10 via line 13 and the aqueous phase is pumped via line 41 to the third equilibration vessel 50. Toluene from still 4 is pumped via line 52 to the third equilibration vessel 50 and the mixture is equilibrated once more and pumped to the final phase separator or decantor 60. After settling, the toluene layer from 60 is returned via line 32 to the second equilibration vessel 30, and the aqueous phase is fed via line 61 to a third still 70 in which PA, H₂O and R₃N are distilled off, condensed and returned via line 12 to the first equilibration vessel 10. The still bottoms from 70 are drained off to yield DA.

In order that those skilled in the art will be better able to understand the practice of the invention, the following examples are given by way of illustration and not by way of limitation.

EXAMPLES

Each of the 9 equilibrations were carried out batchwise as described below. The toluene phases were manipulated as indicated in FIG. II which is self explanatory.

EXAMPLE I

A one liter autoclave was charged with 35.7 g (0.24 mol)phthalic anhydride, 21.84 g (0.04 mol) of the bis imide of formula IIA, hereinafter also identified as "BPA-BI", 67 ml (0.48 mol) triethylamine, 80 ml water, and 320 ml toluene. The autoclave was flushed with N₂, sealed and heated to 200° C. for 2 hours. The autoclave was then cooled and opened. The organic and aqueous phases were separated and samples were taken of each. The aqueous phase was returned to the autoclave together with the next appropriate portion of toluene according to FIG. II. The autoclave was again flushed with N₂, sealed and reheated to 200° C. for 2 hours. The work-up described for the first equilibration was repeated.

The samples of both phases from each cycle were stripped of solvent under vacuum (~25 mm) and 200° C., and analyzed by liquid chromatography (Waters Associates LC, corisol-I column ⅛×2′, solvent=40% $CH_2Cl_2$, 59.5% $CHCl_3$ and 0.5% $Et_2O$; flow rate=2 ml/min, detector=UV, λ254). The results are given in the following tables, where the compositions of the ingredients in the aqueous phase are given in mole percent.

TABLE I

Composition of the Amide-Anhydride Exchange Product (Mole Percent)

| CYCLE I | | | |
|---|---|---|---|
| Equilibration | BI | IA | TA |
| 1 | .02 | 15.2 | 84.8 |
| 2 | .02 | 1.8 | 98.2 |
| 3 | .02 | 0.6 | 99.4 |

| CYCLE II | | | |
|---|---|---|---|
| Equilibration | BI | IA | TA |
| 1 | .02 | 6.0 | 84.0 |
| 2 | .02 | 2.4 | 97.6 |
| 3 | .02 | 0.4 | 99.6 |

| CYCLE III | | | |
|---|---|---|---|
| Equilibration | BI | IA | TA |
| 1 | .02 | 11.2 | 88.8 |
| 2 | .02 | 2.4 | 97.6 |
| 3 | .02 | 0.5 | 99.5 |

The above results show that a biphasic exchange reaction is capable of providing a product having at least ~85 mole percent TA after only 1 equilibration step. Two and three steps resulted in ~98 and ~99.5 mole percent products, respectively.

The third equilibration in all three cycles produced ~18 grams (0.035 mol) of >99 mole percent TA which corresponds to an ~86% overall conversion of the BI of formula II to TA of Formula IV which would be readily dehydrated to the DA of formula I.

Other modifications and variations of the present invention are possible in the light of the above teachings. It is, therefore, to be understood that changes may be made in the particular embodiments described above which are within the full intended scope of the invention as defined in the appended claims.

What is claimed is:

1. A biphasic imide-anhydride exchange process for making aromatic bis(ether phthalic acid) of the formula:

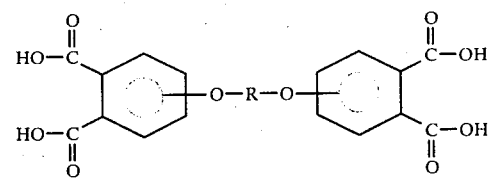

or the anhydride thereof which comprises:
(A) heating a mixture comprising:
(i) aromatic bis(ether phthalimide) of the formula:

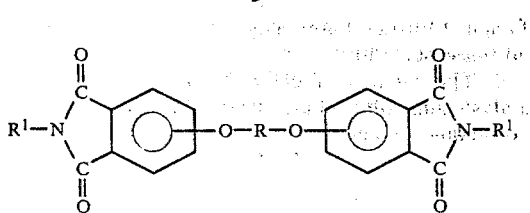

(ii) phthalic anhydride or phthalic acid.
(iii) an exchange catalyst.
(iv) water.
(v) a water-immiscible inert organic solvent to produce an equilibrated liquid biphasic reaction mixture, comprising an aqueous phase having selectively dissolved therein the aromatic bis(ether phthalic acid) formed in the exchange reaction, the catalyst, along with any excess phthalic acid, and an organic phase having selectively dissolved therein, N-organo substituted phthalimide of the formula:

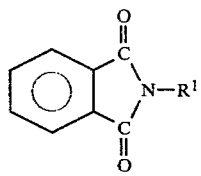

which was also formed in the exchange reaction, together with any unreacted aromatic bis(ether phthalimide), (B) separating the organic phase from the aqueous phase (C) recovering the aromatic bis(ether phthalic acid) from the aqueous phase, and optionally dehydrating it to form the dianhydride, where R is a divalent aromatic radical having from 6–30 carbon atoms and $R^1$ is a monovalent organo radical selected from the class consisting of $C_{(1-8)}$ alkyl radicals, and organic radicals having from 6–20 carbon atoms selected from the class consisting of aromatic hydrocarbon radicals and halogenated derivatives thereof.

2. The process of claim 1 wherein the reaction temperature is between about 170° C.–260° C. and the reaction pressure is between about 200 psi–500 psi.

3. The process of claim 1 wherein the phthalic acid is present at an amount of between about 2–20 moles of the anhydride per mole of aromatic bis(etherphthalimide).

4. The process of claim 1 wherein the exchange catalyst is a trialkyl amine.

5. The process of claim 4 wherein the exchange catalyst is triethyl amine.

6. The process of claim 1 wherein the catalyst is present in a mole ratio of from about 1 to 3 moles of catalyst per mole bis(imide).

7. The process of claim 1 wherein, on a weight basis, the amount of water used is between about 0.01 and 100 parts of the latter per part bis(imide).

8. The process of claim 1 wherein the organic solvent is toluene.

9. The process of claim 1 wherein, on a weight basis, the amount of solvent used is between 0.01 and 100 parts of the latter per part bis(imide).

10. The process of claim 1 wherein $R^1$ is methyl.

11. The process of claim 1 wherein the aromatic bis(ether phthalic acid) is 2,2-bis[4-(3,4-dicarboxyphenoxy)phenyl]propane.

12. The process of claim 1 wherein the bis(ether N-organo substituted phthalimide) is 2,2-bis[4-(3,4-dicarboxy phenoxy)phenyl] propane bis-N-methylimide.

13. A bisphasic imide-anhydride exchange process for making aromatic bis(ether phthalic acid) of the formula:

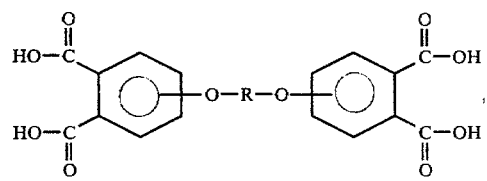

or the anhydride thereof from aromatic bis(ether phthalimide) which comprises:

(A) heating at a temperature of 170°–260° C. and a pressure of 200–500 psi, a mixture comprising:
(i) aromatic bis(ether phthalimide) of the formula:

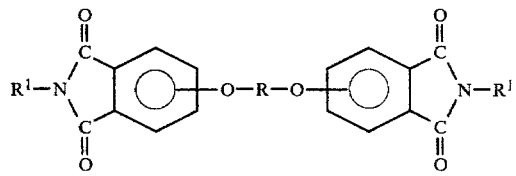

(ii) 2–20 moles phthalic anhydride or phthalic acid per mole of (i).
(iii) 1–3 moles of a trialkylamine exchange catalyst per mole of (i).
(iv) 0.01–100 parts of water per part by weight of (i).
(v) 0.01–100 parts of a water immiscible organic solent per part by weight of (i) to produce an equilibrated liquid biphasic reaction mixture, comprising an aqueous phase having selectively dissolved therein the aromatic bis(ether phthalic acid) formed in the exchange reaction, the trialkylamine catalyst, along with any excess phthalic acid, and an organic phase having selectively dissolved therein, N-organo substituted phthalimide of the formula:

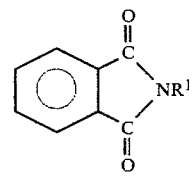

which was also formed in the exchange reaction, together with any unreacted aromatic bis(ether phthalimide), (B) separating the organic phase from the aqueous phase (C) recovering the aromatic bis(ether phthalic acid) from the aqueous phase, and optionally dehydrating it to form the dianhydride, where R is a divalent aromatic radical having from 6–30 carbon atoms and $R^1$ is a monovalent organo radical selected from the class consisting of $C_{(1-8)}$ alkyl radicals, and organic radicals having from 6-20 carbon atoms selected from the class consisting of aromatic hydrocarbon radicals and halogenated derivatives thereof.

14. The biphasic amide-anhydride exchange process of claim 1 further comprising a plurality of equlibration and phase separation steps.

15. The process of claim 1 wherein the reactants catalysts and solvents are recycled and conserved in a continuous manner.

* * * * *